United States Patent
Johnson et al.

(10) Patent No.: US 12,059,383 B2
(45) Date of Patent: Aug. 13, 2024

(54) ASSISTIVE ORTHOTIC DEVICE WITH MOTORS AND SENSORS

(71) Applicant: Icarus Medical, LLC, Charlottesville, VA (US)

(72) Inventors: David T. Johnson, Charlottesville, VA (US); Evan Eckersley, Charlottesville, VA (US); Victoria Harvey, Summit, NJ (US); Benjamin Scire, Hopkinton, MA (US)

(73) Assignee: Icarus Medical, LLC, Charlottesville, VA (US)

( * ) Notice: Subject to any disclaimer, the term of this patent is extended or adjusted under 35 U.S.C. 154(b) by 862 days.

(21) Appl. No.: 17/074,571

(22) Filed: Oct. 19, 2020

(65) Prior Publication Data
US 2021/0030614 A1    Feb. 4, 2021

Related U.S. Application Data

(63) Continuation-in-part of application No. 15/585,968, filed on May 3, 2017, now Pat. No. 10,806,619.

(60) Provisional application No. 62/331,315, filed on May 3, 2016.

(51) Int. Cl.
*A61F 5/01* (2006.01)
*A61H 3/00* (2006.01)

(52) U.S. Cl.
CPC ............ *A61H 3/00* (2013.01); *A61F 5/0125* (2013.01); *A61H 2003/007* (2013.01); *A61H 2201/12* (2013.01); *A61H 2201/1652* (2013.01); *A61H 2230/085* (2013.01); *A61H 2230/50* (2013.01); *A61H 2230/62* (2013.01)

(58) Field of Classification Search
CPC ............ A61F 5/0125; A61F 2005/0139; A61F 2005/0165; A61F 13/048; A61F 13/107; A61F 2013/49096; A61F 5/01; A61F 5/026; A61F 5/028; A61F 2/30; A61F 2002/30624
See application file for complete search history.

(56) References Cited

U.S. PATENT DOCUMENTS

| | | | |
|---|---|---|---|
| 4,602,627 A | 7/1986 | Vito et al. | |
| 7,608,051 B1 | 10/2009 | Nace | |
| 8,376,974 B2 * | 2/2013 | Nace ..................... | A61F 5/0123 601/35 |
| 8,617,254 B2 | 12/2013 | Bisbee, III et al. | |
| 8,622,939 B2 | 1/2014 | Nguyen | |
| 8,652,075 B2 | 2/2014 | Takahashi et al. | |
| 8,663,134 B2 | 3/2014 | Takahashi et al. | |

(Continued)

OTHER PUBLICATIONS

Application No. PCT/US 20/47904, International Search Report and Written Opinion dated Jan. 21, 2021.

(Continued)

*Primary Examiner* — Tarla R Patel
(74) *Attorney, Agent, or Firm* — Woods Rogers Vandeventer Black PLC; Nathan A. Evans (57) ABSTRACT

A motorized tensioning mechanism for orthotic devices, such as a knee brace, wherein the controls for the motorized tensioning mechanism may be manual, automatic, or a hybrid of both. Sensors associated with the orthotic device may inform the user regarding tension or other aspects of the device, and, in cases, may automatically adjust tension in the motorized tensioning mechanism.

26 Claims, 3 Drawing Sheets

(56) References Cited

U.S. PATENT DOCUMENTS

| | | | |
|---|---|---|---|
| 8,784,344 | B2 | 7/2014 | Takahashi et al. |
| 8,814,949 | B2 | 8/2014 | Gramnaes |
| 8,828,095 | B2 | 9/2014 | Mosler et al. |
| 8,882,852 | B2 | 11/2014 | Altobelli et al. |
| 8,926,534 | B2 | 1/2015 | McBean et al. |
| 8,968,223 | B2 | 3/2015 | Ikeuchi et al. |
| 8,968,227 | B2 | 3/2015 | Rokosz et al. |
| 9,022,958 | B2 | 5/2015 | Shimizu et al. |
| 9,248,040 | B2 | 2/2016 | Soderberg et al. |
| 9,820,871 | B2 | 11/2017 | Arabian et al. |
| 10,076,425 | B2 | 9/2018 | Farina et al. |
| 10,792,169 | B2 | 10/2020 | Casler et al. |
| 10,806,619 | B1 | 10/2020 | Johnson |
| 10,835,408 | B2 | 11/2020 | Han et al. |
| 11,026,815 | B2 | 6/2021 | Herr et al. |
| 11,246,723 | B2 | 2/2022 | Harris et al. |
| 11,419,747 | B2 | 8/2022 | Han et al. |
| 11,529,247 | B2 | 12/2022 | Casler, Jr. et al. |
| 11,642,272 | B2 | 5/2023 | Dalley et al. |
| 11,666,463 | B2 | 6/2023 | Goldfarb et al. |
| 11,701,244 | B2 | 7/2023 | Herr et al. |
| 11,707,364 | B2 | 7/2023 | Herr et al. |
| 11,737,903 | B2 | 8/2023 | Blecher |
| 11,759,345 | B2 | 9/2023 | Di Pardo et al. |
| 11,766,348 | B2 | 9/2023 | Armesto et al. |
| 11,786,382 | B2 | 10/2023 | Auberger et al. |
| 11,786,391 | B2 | 10/2023 | LeCursi et al. |
| 2011/0009787 | A1* | 1/2011 | Pallari .................. A61F 5/0127 29/428 |
| 2011/0071452 | A1 | 3/2011 | Auberger |
| 2014/0012173 | A1 | 1/2014 | Newman |
| 2014/0039371 | A1 | 2/2014 | Johnson et al. |
| 2014/0088730 | A1 | 3/2014 | Hansen et al. |
| 2014/0142485 | A1 | 5/2014 | Berry et al. |
| 2014/0200680 | A1 | 7/2014 | Holgate et al. |
| 2014/0221894 | A1 | 8/2014 | Nagasaka |
| 2014/0257156 | A1 | 9/2014 | Capra et al. |
| 2014/0276304 | A1 | 9/2014 | Dollar et al. |
| 2014/0277586 | A1 | 9/2014 | Clausen |
| 2014/0303540 | A1 | 10/2014 | Baym et al. |
| 2014/0330393 | A1 | 11/2014 | Ward et al. |
| 2014/0358053 | A1 | 12/2014 | Triolo et al. |
| 2015/0018972 | A1 | 1/2015 | Albrecht-Laatsch |
| 2015/0150694 | A1 | 6/2015 | Pusch et al. |
| 2015/0150706 | A1 | 6/2015 | Patton et al. |
| 2015/0164660 | A1 | 6/2015 | Will et al. |
| 2015/0173929 | A1 | 6/2015 | Kazerooni et al. |
| 2015/0190248 | A1 | 7/2015 | Vitiello et al. |
| 2015/0190250 | A1 | 7/2015 | Braun et al. |
| 2015/0190923 | A1 | 7/2015 | Seo et al. |
| 2015/0257902 | A1 | 9/2015 | Martin |
| 2015/0297364 | A1 | 10/2015 | Goldfarb et al. |
| 2015/0305895 | A1 | 10/2015 | Boiten et al. |
| 2015/0342759 | A1 | 12/2015 | Hellberg et al. |
| 2016/0051388 | A1 | 2/2016 | Goldfarb et al. |
| 2016/0113831 | A1 | 4/2016 | Hollander |
| 2016/0175134 | A1 | 6/2016 | Ghahfarokhi et al. |
| 2016/0206447 | A1 | 7/2016 | Auberger et al. |
| 2016/0374834 | A1 | 12/2016 | Mosler et al. |
| 2017/0071775 | A1 | 3/2017 | Garrish |
| 2018/0078399 | A1 | 3/2018 | Garrish |
| 2018/0085234 | A1 | 3/2018 | Seifert et al. |
| 2018/0085235 | A1 | 3/2018 | Seifert et al. |
| 2018/0125679 | A1 | 5/2018 | Kaltenborn et al. |
| 2018/0125681 | A1 | 5/2018 | Seifert |
| 2018/0133029 | A1 | 5/2018 | Seifert |
| 2018/0133030 | A1 | 5/2018 | Seifert |
| 2019/0142618 | A1 | 5/2019 | Hyung et al. |
| 2020/0163781 | A1 | 5/2020 | Auberger et al. |
| 2020/0306060 | A1 | 10/2020 | Pappe et al. |
| 2020/0352744 | A1 | 11/2020 | Kaitan et al. |
| 2020/0360169 | A1* | 11/2020 | Kelly .................. A61F 5/0127 |
| 2021/0113415 | A1 | 4/2021 | Seifert et al. |
| 2021/0361455 | A1 | 11/2021 | Eder et al. |
| 2022/0071780 | A1 | 3/2022 | Seifert et al. |
| 2022/0225895 | A1 | 7/2022 | Seifert et al. |
| 2022/0370213 | A1 | 11/2022 | Eder |
| 2022/0370224 | A1 | 11/2022 | Seifert et al. |
| 2022/0387205 | A1 | 12/2022 | Han et al. |
| 2023/0201019 | A1 | 6/2023 | Einarsson et al. |
| 2023/0248548 | A1 | 8/2023 | Auberger et al. |
| 2023/0255802 | A1 | 8/2023 | Gonzalez Vargas et al. |
| 2023/0270570 | A1 | 8/2023 | Hofmann et al. |
| 2023/0277351 | A1 | 9/2023 | Kellum |
| 2023/0293320 | A1 | 9/2023 | Seyr et al. |
| 2023/0310182 | A1 | 10/2023 | Hofmann et al. |
| 2023/0372137 | A1 | 11/2023 | Duke et al. |

OTHER PUBLICATIONS

Tectus product information as downloaded Mar. 22, 2024; https://www.blatchfordmobility.com/en-us/products/orthotics/discover-tectus/tectus/.

* cited by examiner

ASSISTIVE ORTHOTIC DEVICE WITH MOTORS AND SENSORS

CROSS-REFERENCE TO RELATED APPLICATIONS

The present application is a continuation-in-part of and relies on the disclosures of and claims priority to and the benefit of the filing date of U.S. patent application Ser. No. 15/585,968, filed May 3, 2017, which claims priority to and benefit from U.S. Provisional Patent Application No. 62/331,315 filed on May 3, 2016. The disclosures of those applications are hereby incorporated by reference herein in its entirety.

BACKGROUND OF THE INVENTION

Field of the Invention

The current invention provides a motorized tensioning mechanism for orthotic devices, wherein the controls for the motorized tensioning mechanism may be manual, automatic, or a hybrid of both. The tensioning system generates torque across a joint, for example, in the sagittal plane for the knee joint, thereby unloading weight from the joint. The present invention is designed to facilitate the adjusting of the tension stored in an orthotic device using a motorized system. Employing a motorized system in an orthotic device will allow for a more automatic, fine-tuned, and/or accurate adjustment of tension stored in the orthotic device, as well as provide the potential for the motor to store energy upon one particular movement of a joint and release energy upon a different movement of the same joint. Previous motorized tensioning devices oftentimes employ a large and cumbersome motorized portion, and these motorized orthotics are often used solely for rehabilitation purposes. The present invention incorporates a tensioning element to assist the joint and minimizes excess bulk caused by a motor in the orthotic so that the wearer of the device could use the device during physical activity, such as running or contact sports, without being encumbered.

In addition, the current invention describes an interfacial sensor system, including but not limited to electromyography (EMG) or inertial measurement unit sensors, which generate user data that will signal a response by the motorized tensioning mechanism. In parallel, or independently from the communication with the motorized tensioning mechanism, the sensors may communicate with user interfaces through bluetooth or another wireless mechanism to display data on user performance including, but not limited to, movement repetitions, degree of flexion, degree of extension, and position, velocity, and acceleration information.

Description of the Related Art

Typical adjustment of the tension stored in an orthotic device is time consuming, often requiring the skill of a medical provider or fitter—and the user may adjust the tension to a level that is inaccurate to his or her actual needs. Over or under-tensioning an orthotic device can lead to injury, especially in cases where the orthotic device was needed due to prior bodily injury. Additionally, it may not optimally address the medical indications or rehabilitative needs of the user. Wearers of the device may be inclined to hastily adjust the tension stored in the device during physical activity, which would require the user to both pause from his or her activity and potentially lead to inaccurate tensioning in the device. Therefore, a need exists for an improved tensioning adjustment mechanism.

SUMMARY OF THE INVENTION

The orthotic device may be described as an orthotic with an adjustable tensioning element, wherein the adjustable tensioning element can be controlled and adjusted by a mechanical motor-based, pneumatic, or hydraulic system, in aspects. The process by which the adjustable tensioning element may be tightened or loosened is as follows: a sensor receives information about trajectory, orientation, or neuromuscular signal of a limb, which is then compared to an ideal value/values by a processor, which then prompts a controller to take action on a motor, if the received values do not match the ideal ones. The current invention is capable of housing sensors, in a variety of possible orientations, that are capable of detecting the acceleration, velocity, and orientation of the joint/limb, among other features explained herein. In aspects, these sensors, in conjunction with the motorized tensioning system, allow for automatic or partially automatic adjustment of tension in the orthotic device based on the signals received by the sensors. In a preferred embodiment, a system of more than one sensor would be located in or on the orthotic device so that the sensors can average their measurements and report or adjust their positions relative to each other, or instruct the motor to adjust tension (or not adjust tension) in the device. In embodiments, one or two sensors are positioned in the hinge or operatively connected to the hinge of the orthotic device.

The processors may operate automatically, for example based on artificial intelligence, or may have a predetermined range of values as set by the user or a trained professional before use of the orthotic. In an embodiment, the processors function to "check" the values received by the sensors, wherein the values may include but are not limited to the velocity, acceleration, and position of the joint/surrounding limbs, to ensure that the values are within the range of accepted values. The processors may also incorporate data from EMG sensors in addition to or independently of inertial or movement sensors to signal and modulate device tension, which is controlled through a series of feedback loops. In cases where the values detected by the processor lie outside of the range of acceptable values, the controller will initiate a signal to the motor to either loosen or tighten the tension stored in the orthotic in order to restore the received values to their desired range. In one embodiment, the processor and controller may be combined into one physical piece, where the controller sends a signal to the motor to adjust the tension stored in the orthotic device.

Motors may function in conjunction with a unicentric, bicentric, or polycentric joint hinge. If the motor is employed in a unicentric hinge, the motor may be located within the hinge. The motor or motors and power supply can also be contained within the frame of the orthotic or on a patient facing side of the orthotic, depending on the type of hinge present in the orthotic and the articulated joint movement the hinge allows. Concealing the motor within portions of the brace allows for the orthotic to retain a sleek and form-fitting design for the user while maximizing efficiency of the orthotic.

The motors may function in conjunction with the hinge assembly of the orthotic through a direct or indirect system. In the direct system, the motors would directly contact the hinge assembly upon motorization. In an indirect system, the motors would contact the hinge assembly through another component or a possible chain of mechanisms or components upon motorization. In an embodiment, the direct system comprises a crown gear with pinion gears functionally positioned adjacent to the crown gear. Movement of the crown gear would cause rotation of the pinion gears, which would in turn take action on the hinge system. This may be beneficial for an orthotic device used for physical therapy and general patient rehabilitation; for example, a CPM machine used for recovery after anterior cruciate ligament surgery. The motorization of the hinge would allow for the user to perform repetitions of articulated joint movements without the need to physically move the joint before the muscles and ligaments are prepared. Additionally, by optimizing tension and support in real time or near real time, the brace will effectively prevent joint failure, joint buckling, joint collapse, and sudden expected or unexpected changes in the joint. The indirect system may be employed in a variety of methods. For example, in one possible embodiment, the indirect system comprises elastic bands or other elastic component(s) that act as a tensioning element for the brace, wherein tension in the bands can be increased or decreased as the system is engaged, disengaged, or motorized. The indirect system also offers a multitude of orientations and locations for the motors within the orthotic device, because the motors do not need to be located proximally to the hinge, in aspects. Additionally, the indirect system may employ one or multiple motors, wherein the motors may be attached to an end of a tensioning element, such as an elastic band, wire, spring, or combination thereof, that is integrated within the design of the orthotic. Motor configurations may be connected through a system of gears or directly to a spooling mechanism that gathers tension and releases tension in the band in a controllable way.

In embodiments, the orthotic further comprises one or more tensioning element(s), such as an elastic band, wire, spring, hydraulic actuator, pneumatic actuator, or a combination thereof, that is to be released or gathered by one or more of the motors operatively connected to the tensioning element(s). The tensioning element can be anchored to the frame or to a motor anywhere within the frame of the orthotic, and can be placed over a hinge in the orthotic device or entirely or partially located within the frame of the orthotic device. Tension is increased in the tensioning element as the motor adjusts to oppose an articulated joint movement (for example, flexion of the joint), or assist in an articulated joint movement in cases where that may be desired.

In embodiments, the motorized orthotic will further comprise a control system that determines the actions of the motors housed within the orthotic; this control system can be manual (for example, in an embodiment, the user may control how tension is adjusted in the brace), automatic (including control by associated software), or a hybrid of both automatic and manual control. The control systems described herein can function during activity or be set to an "immobilization mode"; for example, to be used if a user might need to immobilize his or her joint after an injury.

The orthotic device described herein is suited for knee and elbow joints, but embodiments can also be adapted to other joints. For example, a shoulder or hip or spine with muscle weakness that needs support may be secured in place by the brace describe herein. The tensioning system may apply forces in a direction such that pain is relieved and functionality is restored.

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention.

DETAILED DESCRIPTION OF VARIOUS EMBODIMENTS OF THE INVENTION

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

All references cited in this specification are hereby incorporated by reference in their entireties.

Embodiment 1—Manual Control System

In one embodiment of the present invention, the control system for the motorized tension system is manual. This system comprises one or more tensioning elements connected to a motor or motors, and the system may optionally comprise sensors. The system of one or more motors may be electronically coupled with a rotatable knob, translational lever, or series of buttons that determines the action of the motor system. For example, pressing a button located on the orthotic or an external device may increase or decrease the tension present in the tensioning element by desired increments or decrements. In embodiments, a user would be able to adjust tensioning by input on an external electronic device, such as a computer or smartphone. For example, computer-implementable instructions on the external electronic device and/or the orthotic would enable a user to set a tension on the external electronic device, the electronic device would send information wirelessly or via wire to the orthotic device (for example, a controller, a processor, or directly to the motor), and the electronic instructions would engage the motor and increase or decrease tension in the connected one or more tensioning element.

Embodiment 2—Automatic Control System

In another embodiment of the present invention, the control system for the motorized tension system is automatic. This system comprises one or more tensioning elements connected to one or more motors, and the motors are in communication directly or indirectly with one or more sensors that sense, for example, the position, velocity and acceleration of the joint, electromyography signal, and/or the orientation of the one or more sensors relative to each other. The sensors may also measure the tension in the one or more tensioning elements. This embodiment relies on the feedback of the sensors directly or indirectly to the motors; for example, the sensors may sense a pattern of movement as "walking" or "running" and may employ more or less tension in the orthotic device based on the pattern detected by engaging and/or controlling the one or more motors. The algorithms used for brace performance may or may not rely on adaptive learning based on patterns and patient requirements.

In embodiments, measurements from the one or more sensors would send information to a controller, a processor, or directly to the one or more motors. In aspects, the processor may located on the orthotic device, on a remote electronic device, such as a computer, smartphone, or the cloud, and the processor may include computer-implementable instructions (e.g., software) that will control what the one or more motors due based on instructions from the processor, the instructions of which are based on input from the one or more sensors. In aspects, a software program housed or stored either on or within the orthotic device, or on an external device connected wirelessly or by wire to the orthotic device, applies machine learning or artificial intelligence to optimize activity of a motor or tensioning mechanism, tensioning of the orthotic device (e.g., joint brace), data processing associated with the orthotic device and associated system, and/or user performance, rehabilitation, or comfort. In other words, computer-implemented steps, software, processes, applications, or programs that affect the device or system performance may be on the orthotic device or a connected electronic device, including a computer, a smartphone, or a server/cloud, by way of example.

In this embodiment of the brace, the user may be allowed to choose whether or not automated tensioning should be enabled in the brace; but, if automated tensioning is enabled, the user should not need to manually adjust tension stored in the orthotic during use of the brace. The controller may be accessed by hardware, a wire, a plug in, a bluetooth system, radio/antenna, or wifi, by way of example, in order to share information with a computer or application for the user's information.

Embodiment 3—Hybrid Control System

In another embodiment of the present invention, the motorized brace comprises a hybrid automatic and manual tensioning system. This system may act by combining elements of embodiments 1 and 2. For example, the user may manually set and adjust a predetermined range of tension in the orthotic device, or a predetermined allowed range of motion as determined by the angle between the sensors in the brace. Once a range has been set, the sensors can provide the motors with real-time information in order to allow the motors to adjust the tension stored in the orthotic device based on the action being performed.

The hybrid control system has the benefit of allowing the user to have more control over qualities of the orthotic depending on the level of activity the user plans to perform while wearing the orthotic. The need for this user input is eliminated with accurate artificial learning of motion patterns as described in embodiment 2. However, users may understandably wish to exercise more autonomy over the orthotic and opt for the hybrid control system.

In embodiments, motors or actuators are operatively connected to one or more tensioning element through a system of gears or another method such as a screw, which can gather or release tension, based on inputs from sensors managed by a controller or processor.

In embodiments, the orthotic device, such as a joint brace or joint wrap, can be used as a non-invasive mechanism for physical therapy or to rehabilitate joint or tissue, or to reduce pain in a wearer, wherein the joint brace or wrap is attached to or contains an apparatus that generates sound waves which cause vibrations that may be pulsed on and off or continuously.

Power Supply

The orthotic will further comprise a power supply, such as batteries, to be contained within the brace, in aspects. Energy generated from resistance in the orthotic, such as resistance to flexion of a joint, may provide the power supply with energy (for example, recharging the power supply). Another possible method of power supply for the orthotic is charging by induction. Power may be supplied by additional internal or external systems, for example solar cells or charging through an external power source. Power can be monitored on the device or through an externally connected device.

In embodiments, the device may comprise one or more batteries optionally contained in or on the orthotic device. The device may further comprise one or more batteries, wherein the one or more batteries are capable of being charged by energy generated from resistance in the one or more motors or actuators acting as generators. In aspects, the orthotic device is capable of generating resistance by changing the system or one or more motors to a generator mode. The device may also further comprise an inductive charging power source, a battery, a solar cell, or an external power source.

Tensioning Meter

The motorized tensioning system may further comprise a tension meter, which may be attached directly or indirectly to the tensioning element or may be embedded in the tensioning element. The tension meter may be used to digitize the amount of tension to provide feedback to the user and as a parameter for the whole system (e.g., including a controller and/or processor). The value of tension may be reported on an external device, such as a smartphone, for the user's information.

Summary Table

| Component | Sensor | Processor | Controller | Motorized Adjustable Tensioning System |
|---|---|---|---|---|
| Function | Record information about positioning, velocity, and acceleration of a joint. Record information about the tension stored in a tensioning element | Compare recorded values from sensor to desired values (set by user or otherwise known to the system) | Signal the motor to adjust the tension stored in the tensioning element to match the desired values | Adjust the tension stored in the tensioning element to match the desired values |

Methods of communication: In aspects, the method of communication between each component is a digital signal that can be converted to analog.

Other Aspects Include:

Aspect 1: An orthotic device comprising a potentiometer, a gear box of a gearing system, and/or one or more servo arms or levers.

Aspect 2: An orthotic device wherein a digital signal activates one or more lights or sounds on the orthotic device to indicate an amount of tension.

Aspect 3: An orthotic device comprising an internal, power source, an external power source, or both.

Aspect 4: An orthotic device comprising piezoelectric material(s) capable of sensing movement, vibration, stress, force, position of the orthotic device, position of a joint or limb, or combinations thereof.

Aspect 5: An orthotic device wherein a tensioning adjustment system assists movement of a joint by resisting either flexion or extension of the joint.

Aspect 6: An orthotic device comprising an external output system, wherein the external output system is capable of adjusting a motorized adjustable tensioning mechanism.

Aspect 7: An orthotic device comprising a display or indicator capable of conveying information about the orthotic device, the one or more tensioning elements, the user, the motorized adjustable tensioning mechanism, or combinations thereof.

Aspect 8: An orthotic device, wherein at least one of the one or more controllers on the device comprise a handle, button, digital touch screen, voice control, or knob that a user can engage in order to make a motorized adjustable tensioning mechanism adjust tension in one or more tensioning element.

Aspect 9: An orthotic device wherein one or more sensors comprise tension measurement sensors capable of sending tension information and/or directly or indirectly controlling a motorized adjustable tensioning mechanism.

Aspect 10: An orthotic device wherein one or more sensors, one or more processors, one or more controllers, a motorized adjustable tensioning mechanism, or combinations thereof, are capable of informing a user and/or a treating medical professional that the orthotic device and/or one or more tensioning element is overloaded.

Figure 1:
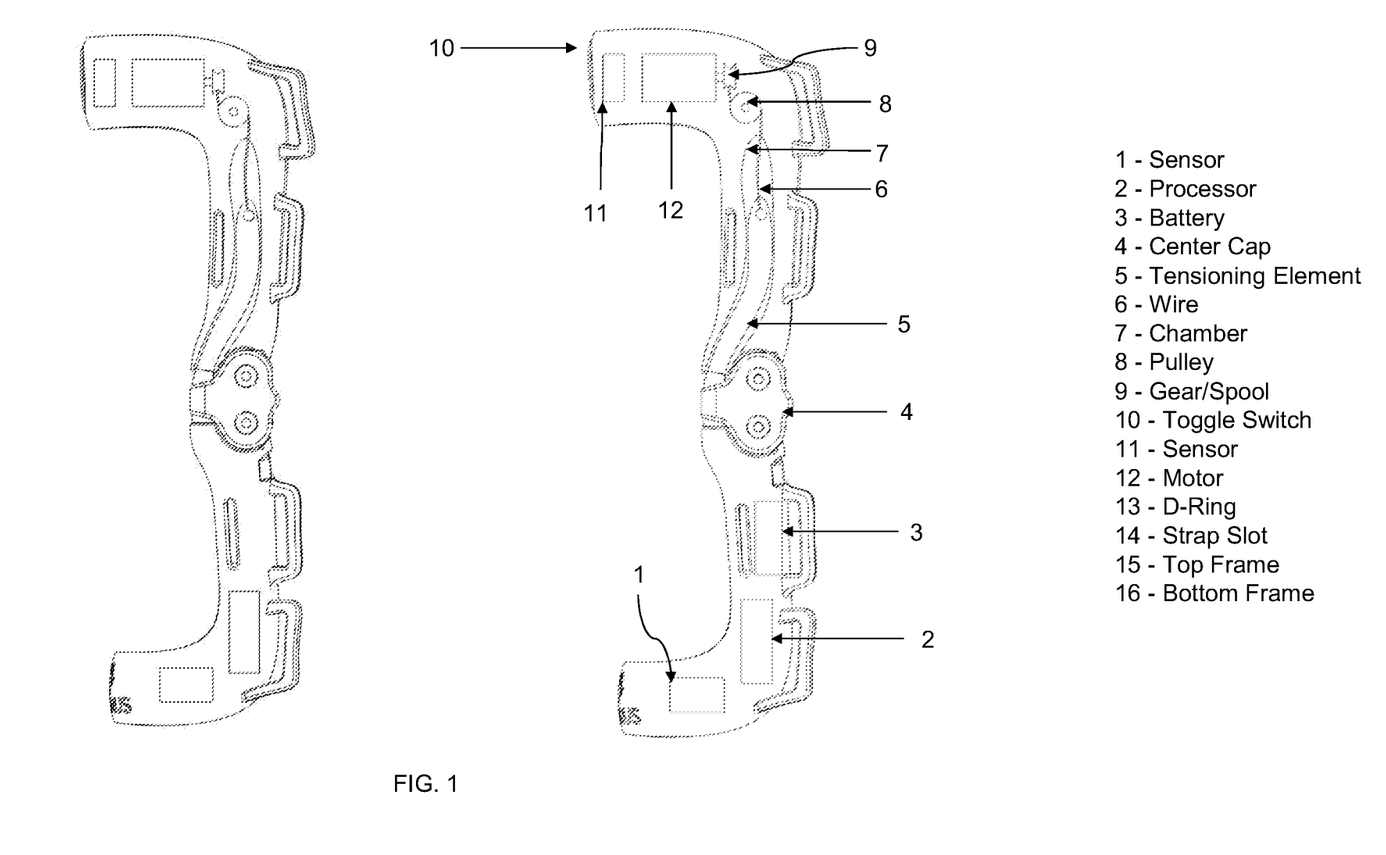
FIG. 1 is a schematic diagram of a depiction of one possible embodiment of a knee brace taught herein.

Turning to the figures, FIG. 1 shows a side view of an orthotic device described herein. In this particular Figure and according to this particular embodiment, a sensor 1 may be located in a portion of the brace, although multiple sensors may be located in more than one location of the brace. In this embodiment, a processor 2 is located on the device although the processor may be located in a wirelessly (or wired) connected electronic device, such as a computer or smartphone. The device may be powered by a battery 3, which in cases may be rechargeable and in cases the energy generated by movement of the device may power the device or battery. A center cap 4 is shown near or one or comprising a hinge for the device where, for example, a joint by bend. A tensioning element 5, in this case a wire(s) or elastic band(s) is shown. In embodiments, the tensioning element may be connected to a wire(s) 6. A chamber in which the tensioning element may reside is shown in 7. In aspects, a pulley 8 is used to adjust tension and direct the wire, and in aspects a gear/spool 9 is further or separately used to adjust tension. In aspects, a toggle switch or other type of switch 10 may be used to turn on/off the device or allow for a user to adjust tension. In the embodiment shown in FIG. 1, the device includes more than one sensor, see sensors at 1 and 11. In this embodiment, a motor 12 adjusts tension in the device. The motor may be adjusted manually (e.g., using a toggle switch, knob, slide, lever, or some other mechanism) or it may be adjusted automatically, in cases using a processor and/or feedback from sensors.

Figure 2:
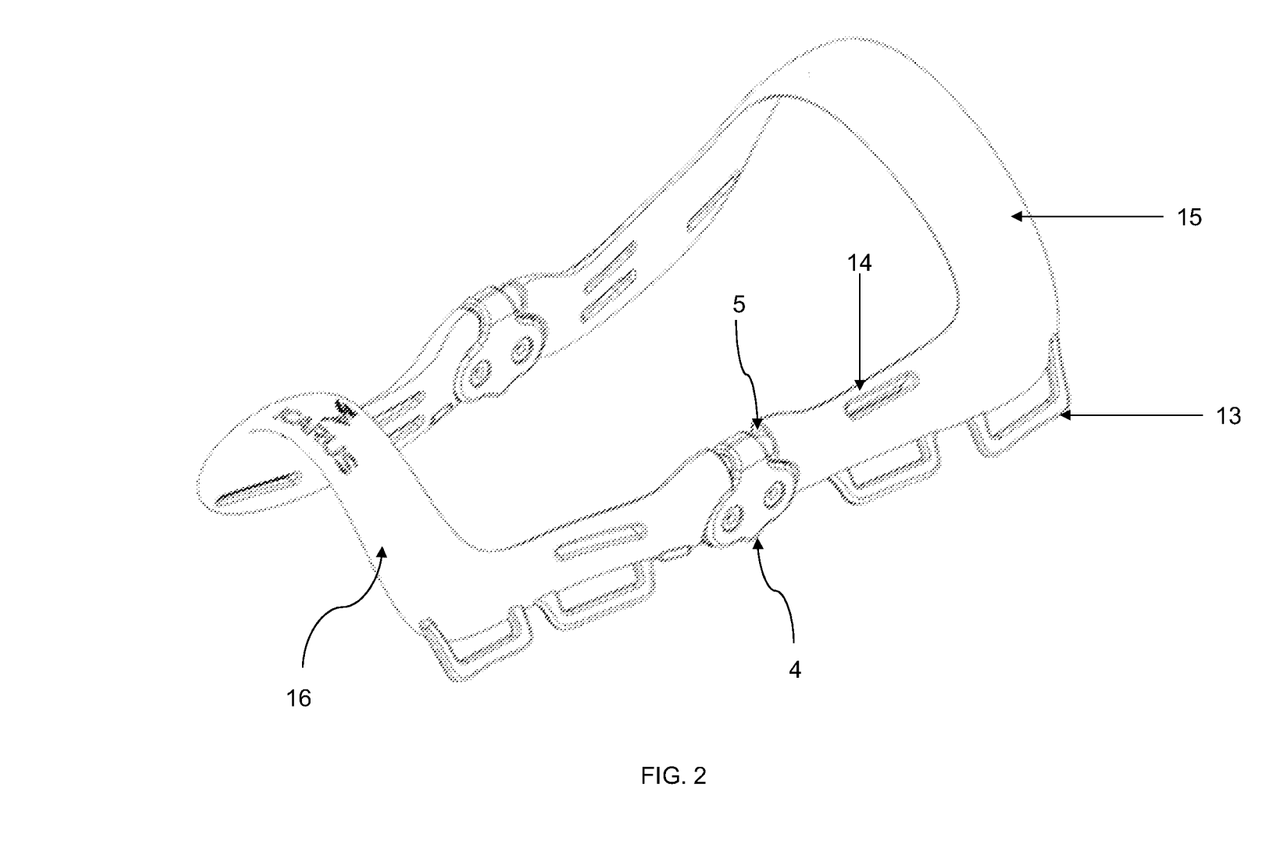
FIG. 2 is a schematic diagram of a depiction of one possible embodiment of a knee brace taught herein.
Figure 3:
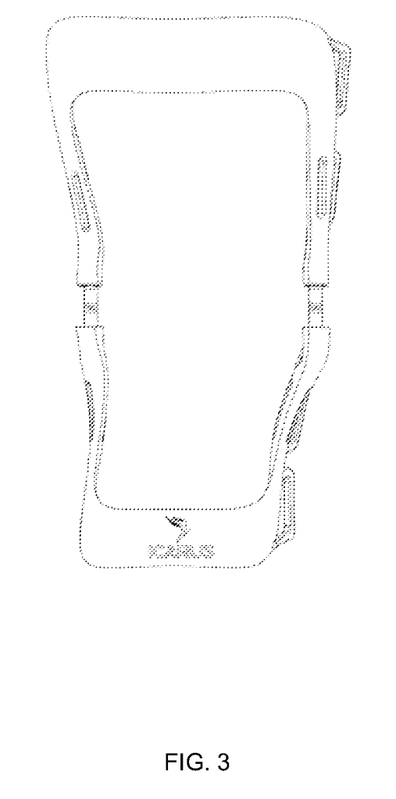
FIG. 3 is a schematic diagram of a depiction of one possible embodiment of a knee brace taught herein.

In FIG. 2, a front and diagonal view of the device is shown, having a lower portion 16 and an upper portion 15. In this embodiment a D-ring 13 may be used to attach a strap to secure the brace to a user's limb, as well as a strap slot 14. In this embodiment, a tensioning element 5 is shown, as well as a center cap 4. In FIG. 3, the device is shown looking at the front of the device straight-on.

Embodiments of the invention also include a computer readable medium comprising one or more computer files comprising a set of computer-executable instructions for performing one or more of the calculations, steps, processes and operations described and/or depicted herein. In exemplary embodiments, the files may be stored contiguously or non-contiguously on the computer-readable medium. Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, steps, operations, algorithms, statistical methods, formulas, or computational routines of this disclosure. The computer or device performing the specified calculations, processes, steps, operations, algorithms, statistical methods, formulas, or computational routines of this disclosure may comprise at least one processing element such as a central processing unit (i.e., processor) and a form of computer-readable memory which may include random-access memory (RAM) or read-only memory (ROM). The computer-executable instructions can be embedded in computer hardware or stored in the computer-readable memory such that the computer or device may be directed to perform one or more of the calculations, steps, processes and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g., software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI) which may be used in conjunction with the computer-executable code and electronic databases. The graphical user interface may allow a user to perform these tasks through the use of text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A motorized orthotic system comprising a joint brace, the joint brace comprising:
   one or more tensioning elements, wherein the one or more tensioning elements generate a force around, within, or between a joint or a body part;
   one or more motors, wherein the one or more motors are capable of increasing and/or decreasing tension in the one or more tensioning elements;
   one or more sensors, wherein the one or more sensors collect information related to the joint brace, the joint, the body part, a user, or combinations thereof; and
   one or more controllers, wherein adjusting the one or more controllers instructs the one or more motors to increase or decrease tension in the one or more tensioning elements; and
   wherein the one or more controllers are adjustable by the user physically interacting with the one or more controllers while wearing the joint brace, or wherein the user can adjust the one or more controllers electronically on a separate electronic device chosen from one or more of a computer, a computer processor, a wearable device, a phone, a smartphone, a server, internet, or cloud, while the user is wearing the joint brace, or wherein the one or more controllers are adjusted automatically or semi-automatically by the system based on the information collected by the one or more sensors.

2. The motorized orthotic system of claim 1, further comprising one or more processors, wherein the one or more processors are located in or on the joint brace, or wherein the one or more processors are located in or on an internal or external electronic device chosen from one or more of a computer processing unit, a circuit board, a computer, a tablet computer, a smartphone, a smartwatch, any wearable smart device, a server, internet, and/or cloud.

3. The motorized orthotic system of claim 1, further comprising one or more processors, wherein the one or more processors are capable of providing the user or a medical professional with information related to a motion of the joint or the limb, wherein the information comprises data about an acceleration, a velocity, a position of the joint or the limb, or combinations thereof.

4. The motorized orthotic system of claim 1, further comprising one or more processors, wherein the one or more processors are capable of providing the user with information regarding electromyography, electrocardiogram electrical heart sensor, an optical heart sensor, blood oxygen level, body temperature, brain activity, other biometric data, or combinations thereof.

5. The motorized orthotic system of claim 1, further comprising one or more processors, wherein the one or more processors include computer-implemented software capable of providing the user with automatic recommendations regarding physical activity.

6. The motorized orthotic system of claim 1, further comprising a motorized adjustable tensioning mechanism, wherein the motorized adjustable tensioning mechanism and/or the one or more tensioning elements comprise or are connected to a tension meter capable of measuring and/or sending information related to a tension in the one or more tensioning elements, wherein the tension meter is optionally attached directly or indirectly to the one or more tensioning elements or embedded within the one or more tensioning elements.

7. The motorized orthotic system of claim 1, wherein at least one of the one or more controllers is controlled by velocity, acceleration, tension, or positioning data sensed by the one or more sensors, and wherein an external output system is capable of tracking and classifying motion patterns of the user of the motorized orthotic system, and wherein the patterns are capable of being used as outputs to control tensioning or use of the motorized orthotic system or to inform the user or a medical provider.

8. The motorized orthotic system of claim 1, further comprising one or more pulleys or gears capable of creating a gearing ratio suitable to adjust an amount of tension within a set span of time.

9. The motorized orthotic system of claim 1, further comprising a motorized adjustable tensioning mechanism, wherein the motorized adjustable tensioning mechanism allows the user to set a predetermined range of tension in the one or more tensioning elements, and wherein the motorized adjustable tensioning mechanism is capable of adjusting the tension in the one or more tensioning elements to maintain the tension within the predetermined range.

10. The motorized orthotic system of claim 1, further comprising a motorized adjustable tensioning mechanism, wherein the one or more sensors comprise one or more tension measurement sensors capable of directly or indirectly instructing the motorized adjustable tensioning mechanism to restrict the user from over-tensioning the one or more tensioning elements.

11. The motorized orthotic system of claim 1, further comprising one or more processors and a motorized adjustable tensioning mechanism, wherein the one or more sensors measure tension in the one or more tensioning elements, wherein the one or more sensors send tension data to the one or more processors, wherein the one or more processors send instructions to the one or more controllers and/or the motorized adjustable tensioning mechanism, and wherein the instructions cause the system to increase or decrease tension in the one or more tensioning elements.

12. The motorized orthotic system of claim 1, wherein at least one of the one or more motors is capable of tightening or loosening a band or strap securing the joint brace to a joint or a limb of the user, or securing a frame of the joint brace, based on input from the one or more sensors or a schedule of use of the joint brace.

13. The motorized orthotic system of claim 1, further comprising one or more processors, one or more actuators, and a motorized adjustable tensioning mechanism, wherein the one or more processors are located on the joint brace or on an external electronic device in communication with the motorized orthotic system, the joint brace, the one or more sensors, the one or more controllers, the one or more motors, the one or more actuators, or the motorized adjustable tensioning mechanism, and wherein the external electronic device is chosen from one or more of a computer, a computer processing unit, a circuit board, a laptop computer, a tablet computer, a phone, a smartphone, a wearable device, a server, internet, cloud, or combinations thereof.

14. The motorized orthotic system of claim 1, further comprising one or more processors and a motorized adjustable tensioning mechanism, wherein the one or more sensors, the one or more processors, the one or more controllers, the motorized adjustable tensioning mechanism, or combinations thereof, are capable of automatically adjusting tension in the one or more tensioning elements based on a preset upper and/or lower range of tension.

15. The motorized orthotic system of claim 1, further comprising one or more processors and a motorized adjustable tensioning mechanism, wherein the one or more sensors, the one or more processors, the one or more controllers, the motorized adjustable tensioning mechanism, or combinations thereof, are capable of providing information to the user about tension on the joint brace and/or motion of a limb or the joint, and wherein the information is optionally displayed on the joint brace and/or on an external electronic device chosen from one or more of a computer, a computer processing unit, a circuit board, a laptop computer, a tablet computer, a phone, a smartphone, a wearable device, a server, internet, cloud, or combinations thereof.

16. The motorized orthotic system of claim 1, further comprising one or more processors and a motorized adjustable tensioning mechanism, wherein the one or more sensors, the one or more processors, the one or more controllers, the motorized adjustable tensioning mechanism, or combinations thereof, are capable of sending the user or a medical professional information related to the motorized orthotic system, the joint brace, the tension, the one or more tensioning elements, a hinge of the joint brace, a prescribed treatment, a joint movement, a joint health, an injury, treatment options, electromyography data, electrocardiography, an electrical heart sensor, an optical heart sensor, a blood oxygen level, a body temperature, a brain activity, other neurological information, or combinations thereof.

17. The motorized orthotic system of claim 1, wherein the motorized orthotic system is capable of converting kinetic energy from a joint movement to electricity by having one or more of the one or more motors act as a generator.

18. The motorized orthotic system of claim 1, further comprising one or more processors and one or more actuators, wherein the motorized orthotic system allows for information to communicate between the one or more sensors, the one or more processors, the one or more controllers, the one or more motors, or the one or more actuators, on the joint brace or multiple orthotic devices, or wherein the motorized orthotic system allows for information to communicate between the one or more sensors, the one or more processors, the one or more controllers, the one or more motors, or the one or more actuators on the joint brace and one or more sensors, one or more processors, one or more controllers, one or more motors, or one or more actuators on another orthotic device.

19. The motorized orthotic system of claim 1, wherein the motorized orthotic system dynamically generates a torque to assist the joint based on input from processed information originating from at least one sensor of the one or more sensors.

20. The motorized orthotic system of claim 1, wherein a first sensor of the one or more sensors is in communication with or connected to an upper portion of the joint and wherein a second sensor of the one or more sensors is in communication with or connected to a lower portion of the joint.

21. The motorized orthotic system of claim 1, wherein the motorized orthotic system is capable of generating electric impulses that stimulate muscles to contract to strengthen, repair, or rehabilitate tissue, including strengthening, repairing, or rehabilitating muscles which have become shortened, weakened, or atrophied due to injury or disease, or wherein the motorized orthotic system generates electrical impulses that use transcutaneous electrical nerve stimulation (TENS) to stimulate nerves for managing or blocking pain signals to a brain of the user, or wherein the motorized orthotic system integrates electrical muscle stimulation (EMS or E-STIM therapy) equipment or electromyostimulation (EMS) or neuromuscular electrical stimulation (NMES) equipment that is attached to or integrated within the joint brace.

22. The motorized orthotic system of claim 1, further comprising one or more processors, one or more actuators, and a motorized adjustable tensioning mechanism; wherein the one or more sensors are capable of detecting electromyography or other biometric data, and wherein information about the electromyography or the other biometric data are communicated to the separate electronic device, the one or more processors, and/or the one or more controllers; wherein the information before or after processing is sent to the one or more controllers and/or the motorized adjustable tensioning mechanism; and wherein the one or more motors and/or the one or more actuators associated with the motorized adjustable tensioning mechanism are capable of adjusting a tension in the one or more tensioning elements.

23. The motorized orthotic system of claim 1, further comprising an internal or external data storage unit, wherein the internal or external data storage unit is capable of monitoring sensor data, processing sensor data, controlling tensioning based on sensor data, sending data to connected devices, or combinations thereof, or wherein the internal or external data storage unit stores user data including information related to an amount of tension in the one or more tensioning elements, an amount of tension imparted on the joint, a pressure, a force, a temperature, a velocity, an acceleration, an orientation of a limb or the joint, electromyography data, electrocardiography, an electrical heart sensor, an optical heart sensor, blood oxygen level, body temperature, brain activity, other biometric data, or combinations thereof.

24. The motorized orthotic system of claim 1, wherein the information collected by the one or more sensors includes one or more of an amount of tension in the one or more tensioning elements, an amount of tension applied to the joint by the one or more tensioning elements, an orientation of the body part or the joint, a velocity, an acceleration, a movement, a pressure applied to the joint, and an angle in a bend of the joint or a hinge of the joint brace, and wherein the information collected by the one or more sensors are viewable and/or accessible by the user.

25. A non-transitory computer readable medium comprising program instructions that, when executed by at least one processor, cause the at least one processor to perform a method for adjusting tension applied by one or more tensioning elements to a joint of a user wearing a joint brace, the method comprising:
- using one or more sensors to sense one or more of an amount of tension in the one or more tensioning elements, an amount of tension imparted on the joint by the one or more tensioning elements, an orientation of a limb or the joint, and an angle in a bend of the joint or a hinge of the joint brace, and wherein the one or more of the amount of tension in the one or more tensioning elements, the amount of tension imparted on the joint by the one or more tensioning elements, the orientation of the limb or the joint, and the angle of the bend in the joint or the hinge of the joint brace, are viewable and/or accessible by the user;
- based on data provided by the one or more sensors, automatically adjusting one or more motors in or on the joint brace to increase or decrease tension applied by the one or more tensioning elements to the joint of the user wearing the joint brace;
- providing one or more controllers, wherein adjusting the one or more controllers instructs the one or more motors to increase or decrease tension in the one or more tensioning elements, and wherein the user can use the one or more controllers to change the tension in the one or more tensioning elements while the user is wearing the joint brace; and
- wherein the one or more controllers are adjustable by the user physically interacting with the one or more controllers, or by the user adjusting the one or more controllers electronically on a separate electronic device chosen from one or more of a computer, a computer processor, a wearable device, a phone, a smartphone, a server, internet, or cloud.

26. The non-transitory computer readable medium comprising program instructions of claim 25, wherein the processor is a micro-processor.

* * * * *